United States Patent [19]

Marcilly

[11] 4,210,770
[45] Jul. 1, 1980

[54] PROCESS FOR AROMATIC HYDROCARBON CONVERSION AND CATALYST THEREFOR

[75] Inventor: Christian Marcilly, Houilles, France

[73] Assignee: Institut Francais du Petrole, Rueil-Malmaison, France

[21] Appl. No.: 14,401

[22] Filed: Feb. 23, 1979

Related U.S. Application Data

[62] Division of Ser. No. 842,132, Oct. 14, 1977, Pat. No. 4,151,120.

[30] Foreign Application Priority Data

Oct. 15, 1976 [FR] France .................. 76 31320
Dec. 22, 1976 [FR] France .................. 76 39015

[51] Int. Cl.² .............................................. C07C 3/62
[52] U.S. Cl. ................................. 585/474; 585/475
[58] Field of Search ............................ 585/474, 475

[56] References Cited

U.S. PATENT DOCUMENTS

| 3,629,351 | 12/1971 | Olive et al. | 585/475 |
| 3,671,602 | 6/1972 | Inoue et al. | 585/474 |
| 3,721,717 | 3/1973 | Suld et al. | 585/475 |
| 3,763,260 | 10/1973 | Pollitzer | 585/475 |
| 3,780,122 | 12/1973 | Pollitzer | 585/474 |
| 3,792,098 | 2/1974 | Brandenburg et al. | 585/475 |

*Primary Examiner*—C. Davis
*Attorney, Agent, or Firm*—Millen & White

[57] ABSTRACT

Process for manufacturing a catalyst for hydrocarbon conversion consisting of a mordenite containing less than 0.5% by weight of sodium, having a molar ratio $SiO_2/Al_2O_3$ from 10 to 100 and further containing at least one metal selected from cobalt, nickel, silver and palladium, wherein said metal in incorporated to a mordenite of the sodic form having a molar ratio $SiO_2/Al_2O_3$ close to 10, the major portion of the sodium is eliminated, the resulting catalyst mass is dried from about 50° to 150° C., and then subjected to a first so-called dry calcination between 300° and 700° C., in the presence of a dry, inert or oxidizing gas containing less than 1% by volume of steam, and to a second so-called wet calcination between 250° and 700° C., in the presence of either steam or an inert or oxidizing gas containing at least 3% of steam.

9 Claims, No Drawings

PROCESS FOR AROMATIC HYDROCARBON CONVERSION AND CATALYST THEREFOR

This is a division of application Ser. No. 842,132 filed Oct. 14, 1977, now U.S. Pat. No. 4,151,120.

This invention relates to the catalytic conversion of aromatic hydrocarbons. More precisely, it is concerned with the dismutation of alkyl aromatic hydrocarbons such as toluene, so as to produce benzene and xylenes, or the transalkylation of alkylaromatic hydrocarbons, such as toluene and trimethylbenzene, to produce xylenes.

It is an object of this invention to provide a new process for preparing a catalyst for toluene dismutation and/or toluene and $C_9^+$ aromatic hydrocarbons transalkylation, of high activity and selectivity and having an improved stability as compared to the catalyst of the prior art. This catalyst for converting hydrocarbons consists of a mordenite calcined in the presence of steam, in which the molar ratio $SiO_2/Al_2O_3$ is from about 10 to 100, preferably from 10 to 50, and having a content of less than 0.5% by weight of sodium ions and preferably less than 0.3% by weight of sodium ions.

The catalyst used according to this invention is a mordenite containing ions of one or more metals selected from cobalt, nickel, silver and palladium. When the selected metal is nickel, the mordenite may also advantageously contain copper.

Many dismutation and transalkylation catalysts have already been described in the prior art. The most efficient contain zeolites as the base, and more particularly, the so-called "wide pore" mordenite in its hydrogen form, as described in U.S. Pat. No. 3,506,731. In the U.S. Pat. Nos. 3,281,483 mentions mordenites essentially exchanged with nickel or silver ions, 3,780,121 includes a statement relating to a mordenite exchanged with ions of group IB metals and characterized by a molar ratio $SiO_2/Al_2O_3$ in the range from 12 to 80, 3,629,351 also concerns a mordenite containing ions of metals from groups IB, VA, VIA, VIIA and VIII, 3,476,821 claims the use of a mordenite containing a sulfurized metal from group VIII and having preferably a molar ratio $SiO_2/Al_2O_3$ higher than 20. However none of these patents mentions or even suggests the particular technique of calcination under wet atmosphere according to the present invention, said technique being strictly necessary during the preparation of the catalyst, in order to obtain a catalyst having the simultaneous properties of being active, stable during time and, overall, very selective in the aromatic hydrocarbon dismutation or transalkylation reactions. Whereas a wet calcination technique is described in 3,720,726 for a mordenite used in sodium form or hydrogen form, this technique differs from the present technique and is clearly less efficient for mordenites containing cobalt, nickel, silver and/or palladium.

The preparation of the catalyst and particularly the calcination step in the presence of steam according to the methods of the present invention, leads to catalyst formulas resulting in substantially improved performances, particularly as concerns activity, selectivity and stability during time, as compared with the catalysts prepared according to the methods of the prior art as exemplified in the above-mentioned patents.

The zeolite used as the base for the preparation of the catalyst of the invention, is the so-called "wide pore" mordenite of sodium form as, for example, that available in the trade under the name of Zeolon Na, manufactured by NORTON Society. This mordenite has a molar ratio $SiO_2/Al_2O_3$ substantially equal to 10. This mordenite, which will be referred to hereinafter as Na-M, has pore openings of about from 7 to 8 Angströms, which makes it possible for aromatic molecules such as polymethylbenzene hydrocarbons having up to 12 carbon atoms per molecule, for example, to fit in the pores.

For the manufacture of the catalyst of the invention, it is first necessary to extract, as above-mentioned, the major part of the sodium ions of the "wide pore" mordenite Na-M and to replace these ions with one or more of the following ions: $Co^{++}$, $Ni^{++}$, $Ag^+$ and $Pd^{++}$.

It is known that the most common method for obtaining the protonic form (as "hydrogen" form) which will be referred to as HM, consists of treating the zeolite of sodic form Na-M in an aqueous solution of an inorganic salt. It is also known that, in order to have the mordenite exchanged with ammonium ions, which will be referred to as $NH_4$-M, the solid is generally allowed to remain in an aqueous solution of ammonium salt.

In order to obtain the mordenite exchange with at least one of the metals selected from Co, Ni, Ag and/or Pd, it is possible to directly exchange the sodium ions of the mordenite Na-M with the metal ions selected from cobalt, nickel, silver and palladium, which are to be introduced. It is also possible to exchange the sodium ions first with $H^+$ ions or with $NH_4^+$ ions and, subsequently, to introduce the desired metals either by ionic exchange or by the so-called dry impregnation (without excess of solution) or by impregnation with an excess of solution. When the desired catalyst must contain several of these metals (Co, Ni, Ag, Pd), the latter may be introduced either each in the same manner or each according to a different method. In the case where the operation is conducted by ion exchange, the various metal cations may be introduced either simultaneously in a single or several operations of cation exchange, by means of solutions containing in admixture several or the all the cations, or successively, by a series of exchanges, each involving a single type of cation. When the metal which is destined to replace the sodium is expensive, this being for example the case of silver, it will be preferable, in order to reduce the cost, to preliminarily exchange the sodium with ammonium ions.

The above mentioned treatment for the preparation of HM mordenite in acid solution has in fact, two separate effects: on the one hand, an attack of the aluminosilicate lattice occurs which results in an extraction of the aluminum atoms and, consequently, in an increase of the ratio Si/Al of the frame; on the other hand, cations of the zeolite are replaced by protons.

This attack of the lattice increases in importance as the treatment is lengthened longer, and as the acid concentration and the temperature of the solution is increased. By such a treatment, it is possible to prepare mordenites of reduced aluminum content having a molar ratio $SiO_2/Al_2O_3$ higher than 10 or even higher than 1,000. It is known that such mordenites of low aluminum content have acid properties different from those of the normal mordenite HM; a maximum acidity is generally obtained for values of the molar ratio $SiO_2/Al_2O_3$ in the range from 10 to 100. It is possible to introduce in the structure of such mordenites of low aluminum content, cations of the selected metals (Co, Ni, Ag, Pd) according to techniques similar to those described above.

The total ion contents of the desired metals in the mordenite may be from 0.01 to 25% by weight, but the preferred contents are from 0.1 to 8% by weight for cobalt and nickel, from 0.2 to 18% by weight for silver and from 0.01 to 5% by weight for palladium.

When the metal is nickel (clearly more hydrogenolyzing than silver, cobalt and palladium), it is possible to add from 0.001 to 1% by weight of copper to the mordenite; as a matter of fact, it has been observed that copper, combined with nickel, contributes to the disappearance of the hydrogenolyzing properties (which result, for example, in methane formation) which may be caused by nickel after calcination under wet atmosphere.

The highest values correspond to contents which cannot always be obtained by ion exchange. Thus the maximum cation exchange rate of 100% corresponds, with nickel, to 7.5% by weight of metal and, with silver, to about 23% by weight. Moreover, the exchange rate of 100% is not always achievable in practice: with nickel, for example, it is not possible to introduce more than about 3% by weight of metal. Values higher than these maximum contents could not therefore be obtained except by impregnation.

Whatever may be the method used, either by ion exchange or impregnation, a relatively substantial amount of the metal ions present in the solid is not fixed to the latter but remains in the form of cations in the solution filling the pores. During the drying or the calcination, the cations tend to be collected and result in the formation of more or less large crystallites of metal oxides or hydroxides which will be located in the macroporosity. Those oxides may then be reduced to the metal state in the presence of hydrogen at high temperature. It can be observed, for example, that crystallites of nickel having a size of about 200–300 Angströms are present in the reduced Ni mordenite. These metal crystallites are responsible for the occurrence of reactions which are highly undesirable for the dismutation, such as:

hydrogenation of aromatics to naphthenes,
hydrogenolyzis with formation of methane and ethane,
coke formation.

The parasitic hydrogenation of aromatics is a very troublesome reaction since it results in the occurrence, in the benzene cut, of substantial amounts of saturated products which may require the performance of an extractive distillation in addition to the conventional distillation, in order to obtain a very pure benzene, in particular free of cyclohexane. The parasitic hydrogenolysis is responsible for a loss of aromatic rings and accordingly for a decrease of the yield in aromatics of the operation. Finally, the parasitic formation of coke may result in a clogging of the micropores of the zeolite and therefore in a very rapid drop of activity of the latter.

On the contrary, these undesirable reactions do not occur at all, or at least are reduced to an acceptable level, when the metal or metals produced in the solid, are dispersed to an almost atomic state in the zeolite structure. In order to avoid, or at least to reduce, the collection of the metals in the form of oxides crystallites which, after reduction, become metal crystallites, it has been suggested, in various patents, to proceed with particular care during certain steps of the mordenite preparation. It has thus been proposed to control the pH of the exchange solutions in order to avoid the formation of hydroxide microprecipitate at the surface of the zeolite, $NH_4$ form for example, whose reaction in solution is very slightly basic (pH of about 7 to 8.5). It has also been proposed to conduct that exchange at temperatures from 80° to 150° C., so as to introduce a larger amount of cations in the structure, and to proceed to a very careful washing of the solid after the ion exchange, so as to progressively remove all the cations remaining in solution (see French Pat. No. 2,033,853).

These various precautionary measures actually result in a significant improvement of the catalyst performances but, however, do not result in such a conclusive improvement as that obtained according to the invention. As a matter of fact, even a very severe control of the pH does not always permit an avoidance of the collection of polyatomic species at the surface of the solid. Thus, in the case, for example, of nickel, the slope of the curves of neutralization, by ammonia, of nickel nitrate solutions, seems to indicate a condensation of the cations in solution resulting in the formation of a polycationic species which, when neutralizing a negative site of the solid, already constitutes the starting of a collection. Moreover, a careful washing of the solid cannot be performed on a mordenite impregnated either with an excess of solution or not, without the liability of losing all of the advantage of this operation, (this advantage being of making possible the introduction of a metal amount greater than that possible by simple ionic exchange). The impregnation method thus results unavoidably in the formation of large crystallites of metal oxide or of metal within the macroporosity and, consequently, in the production of catalysts of low selectivity and low stability. Moreover, a washing, even very careful, of the exchanged zeolites does not completely avoid the formation of these large crystallites. These metal crystallites may constitute crystallization nucleii on which still dispersed metal atoms are liable to become agglomerated and which migrate in the structure during the reaction under the effect of the temperature. This latter phenomenon may also be responsible for the deactivation of the catalyst.

In view of all these problems, each step of the preparation of the zeolite catalyst is important and must be carried out with care. However, all these steps have not the same importance and only a few number thereof are really key points in the preparation since they are, for the most part, responsible for the obtainment of the optimal properties of the catalyst; even in some cases, they can compensate for certain imperfections obtained in the course of the preceding steps.

It has thus been discovered, according to the present invention, that the calcination of the catalyst is a fundamental step of the preparation and that it permits, when properly carried out, the production of catalysts which are simultaneously active, selective and stable during time, from mordenites exchanged and roughly washed or impregnated with a solution of a metal salt. As a matter of fact, it has been made apparent that, when the calcination is carried out according to a form of procedure which will be defined below, in neutral or oxidizing atmosphere and in the presence of steam at temperatures not in excess of 700° C., the resulting catalysts do not suffer from the above-mentioned drawbacks relating to stability and selectivity, while retaining the advantage of an excellent activity.

Precautionary measures must be taken during the calcination in the presence of steam. Thus, it has been observed that for mordenites, containing cobalt, nickel, silver or palladium, it is not proper (after a preliminary drying of the catalyst at 50° to 150° C.), to proceed directly to a calcination in wet atmosphere. As a matter of fact, it has been observed for example, that after a preliminary drying between 50° and 150° C., a direct treatment of a Ni-M or Co-M or Ag-M or Pd-M zeolite with steam or with a gas containing the same, produces a grey-black coloured solid which, after conventional reduction with hydrogen at 450° C., has a very poor selectivity in the dismutation process: a very substantial degradation of the toluene, of the order of from 30 to 70%, by hydrogenation or hydrogenolysis is observed under the usual conditions of the test (420° C.—30 bars—$H_2/HC=5$—VVH=4).

It has also been observed that for mordenites containing nickel, cobalt, silver and/or palladium, it is not proper to proceed as described in U.S. Pat. No. 3,720,726, i.e. to dry the catalyst and then to complete the manufacturing process first by a calcination in wet atmosphere and then by calcination in dry atmosphere. This method is only suitable for the form Na-M.

On the contrary, it is more convenient to subject the zeolites Ni-M, Co-M, Ag-M or Pd-M to the following steps in successive order:

(a) a drying of a few hours (from 2 to 15 hours for example) at a temperature about from 50° to 150° C., generally under atmospheric pressure;

(b) a so-called "dry" calcination, between 300° and 700° C., in the presence of a dry gas, either inert (nitrogen) or oxidizing (preferably air) containing less than 1% by volume of steam (dew point lower than 7° C. in the case of air) and preferably less than 0.25% by volume of steam (dew point lower than $-10°$ C. in the case of air) and, then (c) a so-called "wet" calcination.

The solid obtained as final product has a pale beige color and exhibits catalytic properties (activity, selectivity, stability) which are improved as compared to those of Ni-M, Co-M, Ag-M, Pd-M mordenites, obtained according to other methods.

The so-called "wet" calcination, of the present invention, is performed by treatment with an atmosphere containing steam and optionally at least one other gas, either oxidizing or inert. More precisely, the atmosphere used for the so-called "wet" treatment, consists of:

either pure steam or a mixture of steam with an inert gas, such as argon, nitrogen, etc., this mixture containing less than 100% and at least 3% of steam by volume, and preferably, at least 10% of steam by volume;

or a mixture of steam with an oxidizing gas (oxygen, air, gas containing molecular oxygen), this mixture containing at least 3% by volume of steam (and preferably at least 10% by volume) and less than 100% of steam;

or a mixture (a) of steam and (b) of a mixture of an inert gas with an oxidizing gas, the total mixture containing less than 100% and at least 3% by volume of steam, and preferably at least 10% by volume of steam.

It will be observed that the value of 3% by volume is higher than that corresponding to air saturated with steam at 20° C. (dew point=20° C., steam pressure=17.5 mm of mercury, percent water in air by volume=2.3%). This treatment with steam or with a gas containing the same, is performed between 250° and 700° C., preferably between 300° and 650° C. or, still preferably, between 350° and 600° C., under a pressure from 0.1 to 50 bars, preferably from 0.5 to 10 bars, during periods from 1 minute to 10 days, according to the temperature, the pressure and the atmosphere selected for the treatment.

It will be observed that the wet treatment may directly follow the calcination under dry atmosphere (i.e. without intermediary cooling step) or may be separated from said dry calcination by a cooling, either slowly (under scavenging with a neutral or oxidizing gas), or sudden (by means of a cooled gas or by contact of the hot solid with cold water for example). The catalyst may thus be cooled down to any temperature, for example around ambient temperature.

The catalyst which, on the one hand, has been subjected to a wet treatment according to the method of the present invention and, on the other hand, has been subjected to a conventional reduction with hydrogen, for example between 300° and 500° C., under 1 to 10 bars, for 1 to 10 hours, may be used in the dismutation reactions of toluene to benzene and xylenes and transalkylation reactions of toluene and trimethylbenzenes to xylenes under the following conditions: temperature from 350° to 550° C., preferably from 400° to 500° C., pressure from 10 to 50 bars, preferably from 20 to 40 bars; feed space velocity, expressed in grams of feed charge per gram of catalyst and per hour, from 0.1 to 10 and, preferably, from 0.5 to 4; molar ratio hydrogen/hydrocarbon in the range from 3 to 20 and preferably from 5 to 14.

The following non limitative examples illustrate the invention.

EXAMPLE 1

The object of this experiment is to prepare mordenites exchanged with $NH_4^+$ or $H^+$ ions. The two mordenites $M_1$ ($NH_4$-M) and $M_2$(H-M) are prepared as follows:

$M_1$ ($NH_4$-M): 700 g of sodic mordenite Na-M of the zeolon Na type, as extrudates of $1/16^{th}$ of inch, are subjected to four successive exchanges in 3.5 liters of the molar solution in ammonium nitrate, adjusted to a pH 7 by addition of ammonia, at room temperature for 6 hours under stirring. The solid is filtered, washed and dried at 85° C. for 6 hours. Example 3 indicates how calcination of $M_1$ is performed.

$M_2$ (H-M): 200 g of sodium mordenite Na-M, (the same as that used for the preparation of $M_1$) are subjected to two successive exchanges in one liter of a molar solution of ammonium nitrate and then immersed in 2 liters of a 4 N solution of hydrochloric acid at 80° C. for 30 hours. The solid is filtered, washed, and dried at 85° C. for 6 hours. Example 3 indicates how $M_2$ is calcined.

EXAMPLE 2

The purpose of the experiment is to prepare mordenites exchanged with cobalt, nickel or silver $M_3$, $M_4$, $M_5$, $M_6$ and $M_7$. The calcination methods are indicated hereinafter in example 3.

$M_3$ (Co-M): 100 g of uncalcined solid $M_1$ are immersed in 1 liter of a molar solution of cobalt nitrate adjusted to a pH 7 by ammonia addition. The solution is stirred at room temperature for 6 hours.

$M_4$ (Ni-M): 100 g of uncalcined solid $M_1$ are immersed in 1 liter of a molar solution of nickel nitrate, adjusted to a pH 7 by ammonia addition. The solution is stirred at room temperature for 6 hours.

$M_5$ (Ag-M): 100 g of uncalcined solid $M_1$ are immersed in 1 liter of a molar solution of silver nitrate diamine $NO_3Ag\ (NH_3)_2$ of about pH 9. The solution is stirred at room temperature for 6 hours.

$M_6$ (Ni-M): 50 g of uncalcined solid $M_2$ are exchanged with a solution of nickel nitrate according to a technique identical to that of solid $M_4$.

$M_7$ (Ag-M): 50 g of uncalcined solid $M_2$ are exchanged with a solution of silver nitrate diamine according to a technique identical to that of solid $M_5$.

These samples $M_3$ to $M_7$ are all subjected to a drying step at 85° C., for 6 hours, in an air drying oven.

EXAMPLE 3

Calcination of various samples.

4 types of calcination have been performed on various samples, preliminary dried at 85° C., for 6 hours, in an air drying oven:

(1) calcination at 500° C., for 3 hours, under atmospheric pressure, with a very dry air stream (100 l/h), predried over silica-gel and then dried over a molecular sieve 13 X;

(2) direct calcination of the solid under wet air (50% of steam in gaseous volume) with a flow rate of the total gaseous stream of 100 l/h at 500° C. for 3 hours under atmospheric pressure;

(3) calcination under very dry air ($H_2O < 0.1\%$ by volume) at 500° C. for 2 hours under atmospheric pressure (100 l/h), followed with the contact of the solid, at this temperature and under atmospheric pressure, with an atmosphere consisting of 95% of steam and 5% of air, for 2 hours (100 l/h). No cooling is performed between these two calcination steps;

(4) calcination with wet air (50% of steam in gaseous volume) at a total flow rate of the gaseous stream of 100 l/h, at 500° C. for 3 hours under atmospheric pressure, followed with the contact of the solid at 500° C., under atmospheric pressure, with a very dry air stream (500 l/h) ($H_2O < 0.1\%$ by volume), for 2 hours.

The analyzis of the samples $M_1$ to $M_7$ are reported in table I below. For any given sample, the results of the analysis are the same, irrespective of the method selected for the calcination.

TABLE 1

| CATALYST | CATION | $SiO_2/Al_2O_3$ Molar | % by weight Na | % metal by weight |
|---|---|---|---|---|
| $M_1$ | $NH_4$ | 10.9 | 0.30 | |
| $M_2$ | H | 25.1 | 0.12 | |

TABLE 1-continued

| CATALYST | CATION | $SiO_2/Al_2O_3$ Molar | % by weight Na | % metal by weight |
|---|---|---|---|---|
| $M_3$ | Co | 10.9 | <0.30 | 1.9 |
| $M_4$ | Ni | 10.9 | <0.30 | 1.5 |
| $M_5$ | Ag | 10.9 | <0.30 | 16.7 |
| $M_6$ | Ni | 25.1 | <0.12 | 0.8 |
| $M_7$ | Ag | 25.1 | <0.12 | 13.8 |

The various samples $M_1$ to $M_7$ are referred to hereinafter, according to their type of calcination and by the following code: (the letter "d" is used for indicating "dry", the letter "w" for indicating "wet").

$M^d$ for the first type of calcination (dry air), does not conform to the invention.

$M^w$ for the second type (wet air), not conforms to the invention.

$M^{dw}$ for the third type (dry air followed with wet air), conform with the invention.

$M^{wd}$ for the fourth type (wet air followed with dry air), does not conform to the invention.

The following samples have been prepared:
$M_1^d$, $M_2^d$, $M_3^d$, $M_4^d$, $M_5^d$, $M_6^d$, $M_7^d$
$M_1^w$, $M_2^w$, $M_3^w$, $M_4^w$, $M_5^w$
$M_1^{dw}$, $M_2^{dw}$, $M_3^{dw}$, $M_4^{dw}$, $M_5^{dw}$, $M_6^{dw}$, $M_7^{dw}$
$M_1^{wd}$, $M_2^{wd}$, $M_3^{wd}$, $M_4^{wd}$, $M_5^{wd}$ The so-prepared catalysts, before being used, are subjected to a reduction with hydrogen at 450° C., for 2 hours and under 1 bar.

All the catalysts are then subjected to a test of toluene dismutation under the following conditions:
T°C.=420
P bars=30
feed space velocity=5 g of toluene/hour and g of catalyst
molar ratio $H_2/HC = 5$ The results of the catalytic tests are reported in the following sets of tables 2 to 8. These various tables show the evolution, during time, of the total conversion by weight of toluene, of the loss, in percent by weight, of aromatics, of the content, in percent by weight, respectively of benzene and of $C_8$ aromatics in the total of aromatics and of the content, in percent by weight, of ethylbenzene in $C_8$ aromatics. The activity is shown by the conversion rate, the selectivity by the loss in aromatics and also by the amount of benzene and $C_8$ aromatics in the aromatic fraction.

EXAMPLE 4

Results of tests with catalysts $M_1^d$ to $M_7^d$, calcinated under very dry air atmosphere.

These results are reported in tables 2, 3 and 4 below.

TABLE 2

| Time (h) | Conversion rate | | Loss of aromatics | | Benzene | | $C_8$ Aromatics | | Ethylbenzene in $C_8$ aromatics | |
|---|---|---|---|---|---|---|---|---|---|---|
| | $M_1^d$ | $M_2^d$ | $M_1^d$ | $M_2^d$ | $M_1^d$ | $M_2^d$ | $M_1^d$ | $M_2^d$ | $M_1^d$ | $M_2^d$ |
| 1 | 22.1 | 25.2 | 5.1 | 7.9 | 7.2 | 7.4 | 8.3 | 8.4 | 2.7 | 3.5 |
| 3 | 19.0 | 20.1 | 3.7 | 5.1 | 6.5 | 6.0 | 7.4 | 6.9 | 2.1 | 3.1 |
| 10 | 15.5 | 11.3 | 2.9 | 4.3 | 5.3 | 2.9 | 6.1 | 3.4 | 1.9 | 3.1 |
| 30 | 10.1 | 4.8 | 2.9 | 2.2 | 3.0 | 0.7 | 3.4 | 0.8 | 1.7 | 2.8 |

TABLE 3

| TIME (h) | Conversion rate $M_3^d$ | $M_4^d$ | $M_5^d$ | Loss of Aromatics $M_3^d$ | $M_4^d$ | $M_5^d$ | Benzene $M_3^d$ | $M_4^d$ | $M_5^d$ | $C_8$ Aromatics $M_3^d$ | $M_4^d$ | $M_5^d$ | Ethylbenzene in $C_8$ aromtics $M_3^d$ | $M_4^d$ | $M_5^d$ |
|---|---|---|---|---|---|---|---|---|---|---|---|---|---|---|---|
| 1 | 20.1 | 26.2 | 25.9 | 9.7 | 10.4 | 7.2 | 4.4 | 6.7 | 8.0 | 5.0 | 7.7 | 9.1 | 3.4 | 3.6 | 2.9 |
| 3 | 20.1 | 22.8 | 23.1 | 8.4 | 8.6 | 6.6 | 4.9 | 6.0 | 7.0 | 5.7 | 6.9 | 8.0 | 2.8 | 3.3 | 2.5 |
| 10 | 17.2 | 19.1 | 20.5 | 6.8 | 6.5 | 5.1 | 4.4 | 5.3 | 6.5 | 5.1 | 6.1 | 7.5 | 2.8 | 3.1 | 2.2 |
| 30 | 12.8 | 13.2 | 15.5 | 4.3 | 5.5 | 4.3 | 3.6 | 3.2 | 4.7 | 4.1 | 3.7 | 5.4 | 2.1 | 2.7 | 1.9 |

TABLE 4

| TIME (h) | Conversion rate $M_6^d$ | $M_7^d$ | Loss of Aromatics $M_6^d$ | $M_7^d$ | Benzene $M_6^d$ | $M_7^d$ | $C_8$ Aromatics $M_6^d$ | $M_7^d$ | Ethylbenzene in $C_8$ aromatics $M_6^d$ | $M_7^d$ |
|---|---|---|---|---|---|---|---|---|---|---|
| 1 | 31.7 | 29.4 | 10.7 | 9.2 | 9.0 | 8.6 | 10.2 | 9.8 | 3.5 | 3.8 |
| 3 | 24.7 | 22.8 | 7.1 | 8.1 | 7.5 | 6.2 | 8.6 | 7.1 | 3.1 | 3.6 |
| 10 | 15.5 | 16.1 | 4.8 | 6.0 | 4.5 | 4.3 | 5.2 | 4.9 | 2.7 | 3.2 |
| 30 | 5.5 | 6.4 | 3.1 | 4.2 | 1.0 | 0.9 | 1.1 | 1.1 | 2.5 | 2.9 |

It is observed particularly that mordenites $M_2$, $M_6$ and $M_7$ which have been subjected to an acid treatment, either exchanged or not with transition ions, have a higher initial activity but lose their activity more rapidly during time than the corresponding zeolites which have not been subjected to an acid treatment.

EXAMPLE 5

Results of the tests with catalysts $M_1^w$, $M_2^w$, $M_3^w$, $M_4^w$ and $M_5^w$, directly calcinated under wet air atmosphere.

The results are reported in the following tables 5 and 6:

It is observed that mordenite $M_2^w$ gives substantially the same results as mordenite $M_2^d$.

On the contrary, the nickel mordenites ($M_4^w$), cobalt mordenites ($M_3^w$) and silver mordenites ($M_5^w$), directly calcined in the presence of steam, have a very poor selectivity as compared to the same mordenites calcined under dry air atmosphere, i.e. they result in a substantial loss of aromatics: a strong hydrogenolysis, in particular with a very substantial production of methane, is observed. In the latter case, the low ethylbenzene content of $C_8$ aromatics is to be observed; this result is probably due to the deethylation by hydrogenolysis of ethylbenzene.

TABLE 5

| TIME (h) | Conversion rate $M_1^w$ | $M_4^w$ | Loss of Aromation $M_1^w$ | $M_4^w$ | Benzene $M_1^w$ | $M_4^w$ | $C_8$ Aromatics $M_1^w$ | $M_4^w$ | Ethylbenznene in $C_8$ Aromatics $M_1^w$ | $M_4^w$ |
|---|---|---|---|---|---|---|---|---|---|---|
| 1 | 31.5 | 80.8 | 1.8 | 55 | 12.7 | 10.9 | 14.5 | 12.6 | 1.4 | 1.3 |
| 3 | 29.2 | 81.3 | 1.4 | 56 | 11.9 | 10.7 | 13.6 | 12.3 | 1.3 | 1.1 |
| 10 | 25.1 | 79.7 | 0.9 | 55 | 10.3 | 10.6 | 11.8 | 2.1 | 1.1 | 1.0 |
| 30 | 17.3 | 72.6 | 0.5 | 54 | 7.1 | 7.9 | 8.2 | 9.0 | 1.0 | 0.9 |

TABLE 6

| (h) | Conversion rate $M_2^w$ | $M_3^w$ | $M_5^w$ | Loss of Aromatics $M_3^w$ | $M_5^w$ | Benzene $M_2^w$ | $M_3^w$ | $M_5^w$ | $C_8$ Aromatics $M_2^w$ | $M_3^w$ | $M_5^w$ | Ethylbenzene in $C_8$ Aromatics $M_2^w$ | $M_3^w$ | $M_5^w$ |
|---|---|---|---|---|---|---|---|---|---|---|---|---|---|---|
| 1 | 25.2 | 31.3 | 40.6 | 7.9 | 15.1 | 8.2 | 7.4 | 6.8 | 14.2 | 8.4 | 7.9 | 16.4 | 3.5 | 2.5 | 7.8 |
| 3 | 20.1 | 28.7 | 40.2 | 5.1 | 14.3 | 8.0 | 6.1 | 6.0 | 14.1 | 6.9 | 7.0 | 16.3 | 3.1 | 2.3 | 1.6 |
| 10 | 11.4 | 26.7 | 38.1 | 4.3 | 13.8 | 6.5 | 3.0 | 5.3 | 13.9 | 3.6 | 6.2 | 16.0 | 3.2 | 2.3 | 1.5 |
| 30 | 4.9 | 24.1 | 35.5 | 2.1 | 13.4 | 6.0 | 0.8 | 4.4 | 13.0 | 0.9 | 5.0 | 15.0 | 2.7 | 2.3 | 0.9 |

It is observed a clear improvement of the catalytic properties (particularly activity and selectivity) of the mordenite exchanged with ammonium ions and calcined in the presence of steam ($M_1^w$ as compared to that ($M_1^d$) calcined under dry air atmosphere.

EXAMPLE 6

Results of tests with catalysts $M_1^{dw}$ to $M_7^{dw}$, calcinated first under dry air and then, in the presence of steam.

The results are reported in the following tables 7, 8 and 9.

TABLE 7

| TIME (h) | Conversion rate $M_1^{dw}$ | $M_2^{dw}$ | Loss of Aromatics $M_1^{dw}$ | $M_2^{dw}$ | Benzene $M_1^{dw}$ | $M_2^{dw}$ | $C_8$ Aromatics $M_1^{dw}$ | $M_2^{dw}$ | Ethylbenzene in $C_8$ Aromatics $M_1^{dw}$ | $M_2^{dw}$ |
|---|---|---|---|---|---|---|---|---|---|---|
| 1 | 32.1 | 34.2 | 1.3 | 2.9 | 13.2 | 13.4 | 15.1 | 15.3 | 1.3 | 1.6 |
| 3 | 28.7 | 29.8 | 1.4 | 1.7 | 11.7 | 12.0 | 13.3 | 13.7 | 1.3 | 1.4 |

TABLE 7-continued

| TIME (h) | Conversion rate $M_1^{dw}$ | $M_2^{dw}$ | Loss of Aromatics $M_1^{dw}$ | $M_2^{dw}$ | Benzene $M_1^{dw}$ | $M_2^{dw}$ | $C_8$ Aromatics $M_1^{dw}$ | $M_2^{dw}$ | Ethylbenzene in $C_8$ Aromatics $M_1^{dw}$ | $M_2^{dw}$ |
|---|---|---|---|---|---|---|---|---|---|---|
| 10 | 24.2 | 18.2 | 1.1 | 2.3 | 9.8 | 6.8 | 11.2 | 7.8 | 1.2 | 1.4 |
| 30 | 16.1 | 7.3 | 0.7 | 1.8 | 6.5 | 2.3 | 7.5 | 2.6 | 0.9 | 1.2 |

TABLE 8

| TIME (h) | Conversion rate $M_3^{dw}$ | $M_4^{dw}$ | $M_5^{dw}$ | Loss of Aromatics $M_3^{dw}$ | $M_4^{dw}$ | $M_5^{dw}$ | Benzene $M_3^{dw}$ | $M_4^{dw}$ | $M_5^{dw}$ | $C_8$ Aromatics $M_3^{dw}$ | $M_4^{dw}$ | $M_5^{dw}$ | Ethylbenzene in $C_8$ Aromatics $M_3^{dw}$ | $M_4^{dw}$ | $M_5^{dw}$ |
|---|---|---|---|---|---|---|---|---|---|---|---|---|---|---|---|
| 1 | 39.7 | 43.1 | 42.1 | 4.1 | 4.3 | 3.1 | 5.2 | 16.6 | 16.7 | 17.4 | 19.0 | 19.1 | 1.9 | 1.7 | 1.2 |
| 3 | 36.8 | 41.9 | 41.0 | 3.9 | 4.1 | 2.9 | 14.0 | 16.2 | 16.3 | 16.1 | 18.5 | 18.7 | 1.8 | 1.6 | 1.2 |
| 10 | 32.0 | 38.4 | 38.5 | 2.8 | 3.8 | 2.5 | 12.5 | 14.8 | 15.4 | 14.3 | 16.9 | 17.6 | 1.8 | 1.6 | 1.3 |
| 30 | 26.0 | 31.0 | 31.9 | 2.9 | 3.2 | 2.8 | 9.9 | 11.9 | 12.5 | 11.2 | 13.5 | 14.2 | 1.4 | 1.4 | 1.1 |

TABLE 9

| TIME (h) | Conversion rate $M_6^{dw}$ | $M_7^{dw}$ | Loss of Aromatics $M_6^{dw}$ | $M_7^{dw}$ | Benzene $M_6^{dw}$ | $M_7^{dw}$ | $C_8$ Aromatics $M_6^{dw}$ | $M_7^{dw}$ | Ethylbenzene in $C_8$ Aromatics $M_6^{dw}$ | $M_7^{dw}$ |
|---|---|---|---|---|---|---|---|---|---|---|
| 1 | 45.6 | 43.6 | 6.1 | 6.9 | 16.9 | 15.7 | 19.3 | 17.9 | 2.1 | 2.4 |
| 3 | 40.1 | 38.2 | 5.0 | 6.0 | 15.0 | 13.8 | 17.2 | 19.8 | 2.0 | 2.0 |
| 10 | 36.8 | 32.1 | 3.9 | 4.5 | 14.1 | 11.8 | 16.1 | 13.5 | 1.9 | 1.9 |
| 30 | 27.5 | 29.7 | 3.8 | 3.9 | 10.1 | 11.0 | 11.6 | 12.6 | 1.8 | 1.7 |

The following observations are made:

Calcination under dry air and then in the presence of steam gives results of the same order of magnitude as direct calcination in the presence of wet air with the mordenite exchanged with ammonium ions (comparison of catalysts $M_1^w$ and $M_1^{dw}$). For the mordenite of H form (comparison of $M_2^{wd}$ and $M_2^w$), the calcination under dry air, and then in the presence of steam, has the advantage, as compared to a mordenite directly calcined in the presence of wet air, of giving a better conversion rate at the beginning of the reaction, but this conversion rate decreases considerably after 30 hours of the run.

On the contrary, the type of calcination according to the invention (dry air and then wet air) makes it possible to obtain a much more selective catalyst than that obtained by dry calcination or by direct calcination in the presence of wet air with a mordenite exchanged with nickel, cobalt or silver. The catalysts $M_3^{dw}$, $M_4^{dw}$ and $M_5^{dw}$ are respectively more selective than $M_3^d$, $M_4^d$ and $M_5^d$ or $M_3^w$, $M_4^w$ and $M_5^w$.

EXAMPLE 7

Results of tests with catalysts $M_1^{wd}$, $M_2^{wd}$, $M_3^{wd}$, $M_4^{wd}$, $M_5^{wd}$, first calcinated under wet air and then under dry air.

It has been observed that exactly the same results are obtained than with samples $M_1^w$, $M_2^w$, $M_3^w$, $M_4^w$ and $M_5^w$, which results are reported in tables 5 and 6 above.

EXAMPLE 8

A nickel mordenite $M_8$, doped with copper, is prepared as follows: 100 g of uncalcined solid $M_1$, whose preparation has been described in example 1, are subjected to a ion exchange identical to that used for the preparation of solid $M_4$, in a solution of nickel nitrate. The resulting solid is dried at 200° C. for 4 hours, cooled and subjected to a dry impregnation (without excess of solution) with an adequate volume of an aqueous solution containing 0.1 g of copper in the form of copper nitrate. The resulting product is dried at 85° C. for 6 hours in an air drying oven and then, separated in three equal portions which are respectively calcined according to the three forms of procedure No. 1, 2 and 3, as defined in example 3.

There are thus obtained solids $M_8^d$, $M_8^w$ and $M_8^{dw}$.

EXAMPLE 9

A palladium mordenite $M_9$ is prepared as follows: 100 g of uncalcined solid $M_1$, prepared as in example 1, are immersed in 525 cc of a solution containing 0.0525 mole of palladium nitrate and 10 cc of a 40% HCl solution. The exchange takes place at room temperature for 6 hours under stirring. The product is then washed twice, successively with 1 liter of distilled water, dried at 85° C. for 6 hours and then separated in three equal portions which are respectively calcined as hereabove stated in example 3, according to forms of procedure No. 1, 2 and 3. There are thus obtained solids $M_9^d$, $M_9^w$ and $M_9^{dw}$.

Table 10 below gives analyzes of both solids $M_8$ and $M_9$.

TABLE 10

| CATALYSTS | $SiO_2/Al_2O_3$ Molar | % by weight Na | Additional metal | % by weight metal |
|---|---|---|---|---|
| $M_8$ | 10.9 | <0.3 | Ni | 1.5 |
|  |  |  | Cu | 0.1 |
| $M_9$ | ~10.9 | <0.3 | Pd | 0.1 |

The 6 catalysts obtained are subjected to a test of toluene dismutation under the same conditions as those indicated at the end of example 3.

EXAMPLE 10

Results of the test of catalysts $M_8^d$, $M_8^w$ and $M_8^{dw}$. These results are reported in table 11 below.

TABLE 11

| TIME | Conversion rate | | | Loss of aromatics | | | Benzene | | | $C_8$ aromatics | | | Ethylbenzene | | |
|---|---|---|---|---|---|---|---|---|---|---|---|---|---|---|---|
| (h) | $M_8^d$ | $M_8^w$ | $M_8^{dw}$ | $M_8^d$ | $M_8^w$ | $M_8^{dw}$ | $M_8^d$ | $M_8^w$ | $M_8^{dw}$ | $M_8^d$ | $M_8^w$ | $M_8^{dw}$ | $M_8^d$ | $M_8^w$ | $M_8^{dw}$ |
| 1 | 31.0 | 41.6 | 42.5 | 9.6 | 6.4 | 4.9 | 9.5 | 15.6 | 16.6 | 11.0 | 17.9 | 19.1 | 1.7 | 1.6 | 1.5 |
| 3 | 28.9 | 39.7 | 40.3 | 6.5 | 4.9 | 4.0 | 10.0 | 15.5 | 16.2 | 11.5 | 17.8 | 18.6 | 1.8 | 1.7 | 1.3 |
| 10 | 22.6 | 36.1 | 37.9 | 6.1 | 4.6 | 4.0 | 7.3 | 13.9 | 15.0 | 8.5 | 16.0 | 17.2 | 1.9 | 1.5 | 1.2 |
| 30 | 18.7 | 32.0 | 32.6 | 5.0 | 4.9 | 3.3 | 6.0 | 11.9 | 12.7 | 6.9 | 13.7 | 14.6 | 1.9 | 1.5 | 1.0 |

It will be observed that catalyst $M_8^{dw}$, calcined in dry medium and then in wet atmosphere, has an activity and a selectivity substantially of the same order of magnitude as catalyst $M_4^{dw}$, calcined under the same conditions.

EXAMPLE 11

Results of the tests of catalysts $M_9^d$, $M_9^w$ and $M_9^{dw}$. The results are reported in table 12 below.

TABLE 12

| TIME | Conversion rate | | | Loss of aromatics | | | Benzene | | | $C_8$ aromatics | | | Ethylbenzene | | |
|---|---|---|---|---|---|---|---|---|---|---|---|---|---|---|---|
| (h) | $M_9^d$ | $M_9^w$ | $M_9^{dw}$ | $M_9^d$ | $M_9^w$ | $M_9^{dw}$ | $M_9^d$ | $M_9^w$ | $M_9^{dw}$ | $M_9^d$ | $M_9^w$ | $M_9^{dw}$ | $M_9^d$ | $M_9^w$ | $M_9^{dw}$ |
| 1 | 34.2 | 39.3 | 41.7 | 7.9 | 6.7 | 4.0 | 11.5 | 14.3 | 16.6 | 13.3 | 16.5 | 19.1 | 1.8 | 1.9 | 1.5 |
| 3 | 31.2 | 37.1 | 41.5 | 5.3 | 4.8 | 3.5 | 11.4 | 14.2 | 16.7 | 13.1 | 16.3 | 19.1 | 1.7 | 1.8 | 1.3 |
| 10 | 30.5 | 35.0 | 38.1 | 4.6 | 4.8 | 3.2 | 11.3 | 13.2 | 15.3 | 13.0 | 15.2 | 17.6 | 1.5 | 1.7 | 1.3 |
| 30 | 26.1 | 32.6 | 33.6 | 4.1 | 4.5 | 3.0 | 9.6 | 12.2 | 13.4 | 11.0 | 14.1 | 15.4 | 1.5 | 1.7 | 1.1 |

It is observed that calcination under wet air ($M_9^w$) and particularly that which is preceded with a calcination under dry air atmosphere ($M_9^{dw}$) provides for a clear improvement of the activity and selectivity as compared with the catalyst calcined only dry air.

What I claim is:

1. In a process for dismutation and/or transalkylation or alkylaromatic hydrocarbons in the presence of a catalyst, the improvement which comprises employing a catalyst consisting essentially of a mordenite, said mordenite having a molar ratio of $SiO_2/Al_2O_3$ of from 10 to 100, containing up to 0.5% by weight of sodium, and further containing at least one metal being cobalt, nickel, silver or palladium; wherein said catalyst is produced by the steps of:

(a) eliminating from a mordenite in sodic form having a $SO_2/Al_2O_3$ ratio close to 10 the major portion of the sodium and incorporating at least one metal being cobalt, nickel, silver or palladium;

(b) drying the resultant catalyst mass at a temperature of from 50° to 150° C.;

(c) subjecting the resultant dried catalyst mass to a dry calcination at a temperature of from 300° to 700° C. in the presence of an inert or oxidizing dry gas containing less than 1% by volume of steam; and (d) subjecting the resultant dry-calcined catalyst to a wet calcination at a temperature of from 250° to 700° C. in the presence of at least one gas selected from the group consisting of steam, an inert gas and an oxidizing gas, the inert or oxidizing gas containing at least 3% by volume of steam.

2. The process of claim 1, wherein said at least one metal is present in said catalyst in an amount of from 0.01 to 25% by weight.

3. The process of claim 2 wherein said at least one metal is cobalt or nickel and wherein said amount is from 0.1 to 8% by weight.

4. The process of claim 2 wherein said at least one metal is silver and wherein said amount is from 0.2 to 18% by weight.

5. The process of claim 2 wherein said at least one metal is palladium, and wherein said amount is from 0.01 to 5% by weight.

6. The process of claim 1, wherein said at least one metal is nickel and wherein copper is also added as an additional metal.

7. The process of claim 6, wherein said copper is present in an amount from 0.001 to 1% by weight.

8. The process of claim 1, wherein said process is the dismutation of toluene.

9. The process of claim 1, wherein said process is the transalkylation of toluene and $C_9$ alkylbenzenes.

* * * * *